(12) United States Patent
Cheng et al.

(10) Patent No.: US 9,909,106 B2
(45) Date of Patent: Mar. 6, 2018

(54) RECOMBINANT BACULOVIRUS EXPRESSION VECTOR AND CELL

(71) Applicant: Miami University, Oxford, OH (US)

(72) Inventors: Xiao-Wen Cheng, Oxford, OH (US);
Xin-Hua Cheng, Cincinnati, OH (US);
Tyler A. Garretson, Oxford, OH (US)

(73) Assignee: Miami University, Oxford, OH (US)

( * ) Notice: Subject to any disclaimer, the term of this patent is extended or adjusted under 35 U.S.C. 154(b) by 27 days.

(21) Appl. No.: 14/766,777

(22) PCT Filed: Feb. 14, 2014

(86) PCT No.: PCT/US2014/016355
§ 371 (c)(1),
(2) Date: Aug. 10, 2015

(87) PCT Pub. No.: WO2014/127184
PCT Pub. Date: Aug. 21, 2014

(65) Prior Publication Data
US 2016/0122724 A1 May 5, 2016

Related U.S. Application Data

(60) Provisional application No. 61/764,635, filed on Feb. 14, 2013.

(51) Int. Cl.
C12N 7/00 (2006.01)
C07K 14/005 (2006.01)
C12N 15/86 (2006.01)

(52) U.S. Cl.
CPC .............. *C12N 7/00* (2013.01); *C07K 14/005* (2013.01); *C12N 15/86* (2013.01); *C12N 2710/14022* (2013.01); *C12N 2710/14043* (2013.01); *C12N 2710/14122* (2013.01); *C12N 2710/14143* (2013.01); *C12N 2710/14152* (2013.01)

(58) Field of Classification Search
None
See application file for complete search history.

(56) References Cited

PUBLICATIONS

Cheng, Xinhua. The Effects of AcMNPV fp25k Mutations on Very Late Gene Expression and Virion Occlusion in Insects and Insect Cells, 2012, 139 p., Dissertation Online at https://etd.ohiolink.edu/pg_10?0::NO:10:P10_ETD_SUBID:57784, Abstract Only.*
Baker et al., Protein Structure Predication and Structural Genomics, Science (2001) vol. 294, No. 5540, pp. 93-96.*
Attwood, T. The Babel of Bioinformatics, Science (2000) vol. 290, No. 5491, pp. 471-473.*

(Continued)

*Primary Examiner* — Michelle S Horning
(74) *Attorney, Agent, or Firm* — Jason H. Foster; Kremblas & Foster (57) ABSTRACT

A recombinant baculovirus expression vector or cell comprising an engineered baculovirus fp25k gene with one to three modified or mutated spots, the modified spots comprise the two 7-adenine mononucleotide repeats (MNR) and the $10^{th}$ TTAA site. The invention also provides the method of making the vector and baculovirus.

6 Claims, 3 Drawing Sheets

(56) References Cited

PUBLICATIONS

Cheng, Xin-Hua, et al, Reduction of polyhedrin mRNA and protein expression levels in Sf9 and Hi5 cell lines, but not in Sf21 cells, infected with Autographa californica multiple nucleopolyhedrovirus fp25K mutants, Journal of General Virology, vol. 94, 2013, pp. 166-176.

Giri, Lopamudra, et al, Removal of transposon target sites from the Autographa californica multiple nucleopolyhedrovirus fp25k gene delays, but does not prevent, accumulation of the few polyhedra phenotype, Journal of General Virology, vol. 91, 2010, pp. 3053-3064.

Harrison, Robert L., et al, The Role of the AcMNPV 25K Gene, "FP25," in Baculovirus polh and p10 Expression, Virology, vol. 226, Article No. 0625, 1996, pp. 34-46.

Kelly, Bi, et al, Extended budded virus formation and induction of apoptosis by an AcMNPV FP-25/p35 double mutant in Trichoplusia ni cells, Virus Research, vol. 133(2), 2008, pp. 157-166.

Wu, Dong, et al, Functional analysis of FP25K of Helicoverpa armigera single nucleocapsid nucleopolyhedrovirus, Journal of General Virology, vol. 86, 2005, pp. 2439-2444.

Lo, Huei-Ru and Chao, Yu-Chan, Rapid Titer Determination of Baculovirus by Quantitative Real-Time Polymerase Chain Reaction, Biotechnology Progress—Jan. 2004, pp. 354-360, vol. 20, No. 1, 2004 American Chemical Society and American Institute of Chemical Engineers, published on Web.

\* cited by examiner

PASSAGE IN Hi5 CELLS

PASSAGE IN sf9 CELLS

FIG. 3B

SEQUENCE LISTING

```
<160> NUMBER OF SEQ ID NOS: 12

<210> SEQ ID NO 1
<211> LENGTH: 645
<212> TYPE: DNA
<213> ORGANISM: Autographa californica multiple nucleopolyhedrovirus

<400> SEQUENCE: 1
```

```
atggatcaat ttgaacagtt gattaacgtg tctctgctca agtcgttgat caaaacgcaa     60
atcgacgaaa atgtgtcgga caatatcaag tcgatgagcg aaaaactaaa aaggctagaa    120
tacgacaatc tcacagacag cgttgagata tacggtattc acgacagcag gctgaataat    180
aaaaaaatta gaaactatta tttaaaaaag atttgcgctt tactcgacct aaactttaaa    240
cacgtcatag aatcttcgtt tgacaaaaac cacattgtgg ccaagctgtg tgacgcgacg    300
cgcgctaaag aatggcaaac caagtcgcgc gagcgtcgac ttaaaaattt taatttaaac    360
attaattacg acgggcccgt aaaaatattt gtggccgcca cagcggagca aaagctgtta    420
cttaaaaaaa ctcgcgacgc tctgttgccg ttttacaaat acatttccat ttgtaaaaac    480
ggtgttatgg tgagacgcga cgaaaagagt cgcgtgttta ttgttaaaaa tgagcaaaat    540
atagaatatc tcaaagccaa caaatattac gcttttcata gcgatagcgt cgataatttt    600
gagtctgaaa acgatagcga aaaaatgctt caaaatttaa tttaa                    645
```

```

<210> SEQ ID NO 2
<211> LENGTH: 645
<212> TYPE: DNA
<213> ORGANISM: Artificial Sequence
<220> FEATURE:
<223> OTHER INFORMATION: A recombinant baculovirus expression vector,
      AcP3SDM fp25k
<400> SEQUENCE: 2
atggatcaat ttgaacagtt gattaacgtg tctctgctca agtcgttgat caaaacgcaa     60
atcgacgaaa atgtgtcgga caatatcaag tcgatgagcg aaaaactaaa aaggctagaa    120
tacgacaatc tcacagacag cgttgagata tacggtattc acgacagcag gctgaataat    180
aagaaaatta gaaactatta tttaaaaaag atttgcgctt tactcgacct aaactttaaa    240
cacgtcatag aatcttcgtt tgacaaaaac cacattgtgg ccaagctgtg tgacgcgacg    300
cgcgctaaag aatggcaaac caagtcgcgc gagcgtcgac ttaaaaattt taatttaaac    360
attaattacg acgggcccgt aaaaatattt gtggccgcca cagcggagca aaagctgtta    420
ctgaagaaga ctcgcgacgc tctgttgccg ttttacaaat acatttccat ttgtaaaaac    480
ggtgttatgg tgagacgcga cgaaaagagt cgcgtgttta ttgttaaaaa tgagcaaaat    540
atagaatatc tcaaagccaa caaatattac gcttttcata gcgatagcgt cgataatttt    600
gagtctgaaa acgatagcga aaaaatgctt caaaatttaa tttaa                    645

<210> SEQ ID NO 3
<211> LENGTH: 34
<212> TYPE: DNA
<213> ORGANISM: Artificial Sequence
<220> FEATURE:
<223> OTHER INFORMATION: Primer, pA7-1F
<400> SEQUENCE: 3
cgacagcagg ctgaataata agaaaattag aaac                                 34

<210> SEQ ID NO 4
<211> LENGTH: 39
<212> TYPE: DNA
<213> ORGANISM: Artificial Sequence
<220> FEATURE:
<223> OTHER INFORMATION: Primer, pA7-1R
<400> SEQUENCE: 4
ctaattttct tattattcag cctgctgtcg tgaataccg                            39
```

<210> SEQ ID NO 5
<211> LENGTH: 32
<212> TYPE: DNA
<213> ORGANISM: Artificial Sequence
<220> FEATURE:
<223> OTHER INFORMATION: Primer, pTTAA-F

<400> SEQUENCE: 5
gttactgaag aagactcgcg acgctctgtt gc                               32

<210> SEQ ID NO 6
<211> LENGTH: 31
<212> TYPE: DNA
<213> ORGANISM: Artificial Sequence
<220> FEATURE:
<223> OTHER INFORMATION: Primer, pTTAA-R

<400> SEQUENCE: 6
cgtcgcgagt cttcttcagt aacagctttt g                                31

<210> SEQ ID NO 7
<211> LENGTH: 645
<212> TYPE: DNA
<213> ORGANISM: Artificial Sequence
<220> FEATURE:
<223> OTHER INFORMATION: A recombinant baculovirus plasmid vector
    pUCA7-1

<400> SEQUENCE: 7
atggatcaat ttgaacagtt gattaacgtg tctctgctca agtcgttgat caaaacgcaa    60
atcgacgaaa atgtgtcgga caatatcaag tcgatgagcg aaaaactaaa aaggctagaa   120
tacgacaatc tcacagacag cgttgagata tacggtattc acgacagcag gctgaataat   180
aagaaaatta gaaactatta tttaaaaaag atttgcgctt tactcgacct aaactttaaa   240
cacgtcatag aatcttcgtt tgacaaaaac cacattgtgg ccaagctgtg tgacgcgacg   300
cgcgctaaag aatggcaaac caagtcgcgc gagcgtcgac ttaaaaattt taatttaaac   360
attaattacg acgggcccgt aaaaatattt gtggccgcca cagcggagca aaagctgtta   420
cttaaaaaaa ctcgcgacgc tctgttgccg ttttacaaat acatttccat tgtaaaaac    480 ggtgttatgg tgagacgcga cgaaaagagt cgcgtgttta ttgttaaaaa tgagcaaaat   540
atagaatatc tcaaagccaa caaatattac gcttttcata gcgatagcgt cgataatttt   600
gagtctgaaa acgatagcga aaaaatgctt caaaatttaa tttaa                   645

<210> SEQ ID NO 8
<211> LENGTH: 18
<212> TYPE: DNA
<213> ORGANISM: Artificial Sequence
<220> FEATURE:
<223> OTHER INFORMATION: Primer FP-F

<400> SEQUENCE: 8
atgcatagca atgtcttc                                                18

<210> SEQ ID NO 9
<211> LENGTH: 18
<212> TYPE: DNA
<213> ORGANISM: Artificial Sequence
<220> FEATURE:
<223> OTHER INFORMATION: Primer, FP-R

<400> SEQUENCE: 9

```
tttacgcacc atatacgc                                                    18

<210> SEQ ID NO 10
<211> LENGTH: 645
<212> TYPE: DNA
<213> ORGANISM: Artificial Sequence
<220> FEATURE:
<223> OTHER INFORMATION: 1.5 kbp PCT product of P5 (passaged 5 times) of
      AcP3, showing the 10th TTAA site with a host DNA insertion.

<400> SEQUENCE: 10
atggatcaat tgaacagtt gattaacgtg tctctgctca agtcgttgat caaaacgcaa        60
atcgacgaaa atgtgtcgga caatatcaag tcgatgagcg aaaaactaaa aaggctagaa      120
tacgacaatc tcacagacag cgttgagata tacggtattc acgacagcag gctgaataat      180
aaaaaaatta gaaactatta tttaaaaaag atttgcgctt tactcgacct aaactttaaa     240
cacgtcatag aatcttcgtt tgacaaaaac cacattgtgg ccaagctgtg tgacgcgacg      300
cgcgctaaag aatggcaaac caagtcgcgc gagcgtcgac ttaaaaattt taatttaaac     360
attaattacg acgggcccgt aaaaatattt gtggccgcca cagcggagca aaagctgtta     420
cttaaccgat tcgcgacgc tctgttgccg ttttacaaat acatttccat ttgtaaaaac      480
ggtgttatgg tgagacgcga cgaaaagagt cgcgtgttta ttgttaaaaa tgagcaaaat     540
atagaatatc tcaaagccaa caaatattac gcttttcata gcgatagcgt cgataatttt     600
gagtctgaaa acgatagcga aaaatgctt caaaatttaa tttaa                       645

<210> SEQ ID NO 11
<211> LENGTH: 21
<212> TYPE: DNA
<213> ORGANISM: Artificial Sequence
<220> FEATURE:
<223> OTHER INFORMATION: AcMNPV p34F Primer for real time qPCR

<400> SEQUENCE: 11
cccgtaacgg acctcgtact t                                                 21

<210> SEQ ID NO 12
<211> LENGTH: 28
<212> TYPE: DNA
<213> ORGANISM: Artificial Sequence
<220> FEATURE:
<223> OTHER INFORMATION: AcMNPV p34R primer for real time qPCR

<400> SEQUENCE: 12
ttatcgagat ttatttgcat acaacaag                                          28
```

RECOMBINANT BACULOVIRUS EXPRESSION VECTOR AND CELL

This application claims the benefit of the priority International Application No. PCT/US 2014/16355 filed on 14 Feb. 2014, and by way of the PCT application of U.S. provisional application Ser. No. 61/764,635 filed on 14 Feb. 2013. The entire contents of the above applications are hereby incorporated by reference.

The instant application contains a Sequence Listing which has been submitted in ASCII format (.txt) via EFS-web and is hereby incorporated by reference in its entirety. Said ASCII copy, created on 1 Oct. 2015, is named miamx137_seqlisting.txt and is 4 megabytes in size.

BACKGROUND OF THE INVENTION

1. Field of the Invention

This invention relates generally to a baculovirus expression vector and/or a recombinant baculovirus with an engineered baculovirus fp25k gene with an improved resistance to mutation during the process of producing a desired protein, virus, protein hybrid, or virus hybrid.

2. Description of the Related Art

Baculoviruses in the family of Baculoviridae are insect-specific viruses with a circular dsDNA genome of 80-180 kbp. The typical species of the family is *Autographa californica* multiple nucleopolyhedrovirus_(AcMNPV) that has been extensively studied due to its propensity to replicate in many insect cell lines such as Sf21, Sf9 and High Five (Hi5), which makes the AcMNPV-cell systems particularly useful in baculovirus genetic studies.

The popularity of baculovirus to researchers other than baculovirologists is due to its powerful high exogenous gene expression capability in insect cells commonly known as the baculovirus expression vector systems or BEVS. The high protein expression was first recognized by the formation of large polyhedra of 0.5-15 μm in diameter, consisting of a viral polyhedrin (polh) protein in infected insect cells. The high foreign gene expression yield is recognized by the strong promoter of polh that allows the viral RNA polymerase and some late expression factor (LEF) to initiate transcription at extremely high rates for high foreign gene expression during insect cell infection. Of the many baculoviruses reported, AcMNPV is the first baculovirus that has been used for high yield human beta interferon expression under the control of the strong polh promoter. In addition, for high protein expression, the insect cell lines are also critical. Therefore, the Hi5 cell line was cloned from the embryos of *Trichoplusia ni* and has been used to support high protein expression yield of some genes that leads to be the choice of expressing the major capsid protein L1 of human papilloma-virus (HPV) by the AcMNPV-based BEVS for the production of a high cost prophylactic Cervarix® vaccine to prevent HPV infection-caused cervical cancer by GlaxoSmithKline Biologicals. In addition to Hi5 cells, Sf21 and Sf9 cell lines (a clone of Sf21), derived from pupal ovaries of *Spodoptera frugiperda*, have been used for protein expression in research laboratories and industry.

During protein expression in Hi5 cells using the strong polh promoter-based AcMNPV BEVS, the AcMNPV fp25k gene mutates at a high frequency that leads to down-regulating polh-promoter activities thus a reduction of protein expression by up to 70% compared to that without fp25k mutations (Cheng et al., 2013 J. Gen. Virol 94: 166-176; Harrison et al., 1996 Virology 226: 34-46). Accompanied with the reduced polh promoter activities is the enhanced production of virus in insect cell growth media (Harrison and Summer, 1996 Virology 226: 34-46; Kelly et al., 2008 Virus Res. 133: 157-166; Wu et al., 2005 J. Gen. Virol. 86: 2439-2444). Mutations of AcMNPV fp25k are reported due to slippage replication errors of the two 7-adenine mononucleotide repeats (MNR) and a 287 bp host DNA insertion at the $10^{th}$ TTAA site in Sf21 cells (Cheng et al., 2013 J. Gen. Virol 94: 166-176; Gin et al., 2010 J. Gen. Virol. 91: 3053-3064). Therefore, there are three high mutational "hot spots" in the AcMNPV fp25k gene.

BRIEF SUMMARY OF THE INVENTION

The present invention provides for an improved baculovirus expression vector or a recombinant baculovirus comprising an engineered baculovirus fp25k gene that is more resistant to mutation during cell passaging for protein expression than that of the wild-type (wt) fp25k gene. More specifically, the present invention provides for an engineered *Autographa californica* multiple nucleopolyhedrovirus (AcMNPV) fp25k gene that is mutation resistant. The engineered baculovirus fp25k gene includes one to three modified or mutated spots, preferably three modified spots. These modified spots include the two 7-adenine mononucleotide repeats (A7 MNR) and the $10^{th}$ TTAA site. The first A7 MNR (also referred to as A7-1) is modified or mutated into AAGAAAA, which is then called the modified A7-1 MNR. The second A7 MNR (also referred to as A7-2) and the $10^{th}$ TTAA site are collectively modified or mutated to CTGAAGAAGA from CTTAAAAAAA, which are collectively called the modified A7-2 MNR/$10^{th}$ TTAA site. The most preferred embodiment includes all three modified spots, with the modified A7-1 MNR being AAGAAAA, and the collectively modified A7-2 MNR/$10^{th}$ TTAA site being CTGAAGAAGA, which can be exemplified by an engineered baculovirus fp25k gene with a nucleic acid of SEQ ID NO. 2.

BRIEF DESCRIPTION OF THE SEVERAL VIEWS OF THE DRAWINGS

FIG. 1C has two partial histograms of DNA sequencing reactions: one is 1.2 kbp PCR product of AcP3 P0 (no passage) (a nucleic acid of SEQ ID NO. 1), showing the wt $10^{th}$ TTAA site; the other is 1.5 kbp PCR product of P5 (passaged 5 times) of AcP3, a nucleic acid of SEQ ID NO.

10, showing the 10th TTAA site with a host DNA insertion (*). The putative transposition site is underlined.

In describing the preferred embodiment of the invention which is illustrated in the drawings, specific terminology will be used for the sake of clarity. However, it is not intended that the invention be limited to the specific term so selected and it is to be understood that each specific term includes all technical equivalents which operate in a similar manner to accomplish a similar purpose. For example, the words connected or terms similar thereto are often used. They are not limited to direct connection, but include connection through other elements where such connection is recognized as being equivalent by those skilled in the art.

DETAILED DESCRIPTION OF THE INVENTION

Broadly, the present invention provides for an improved baculovirus expression vector or a recombinant baculovirus comprising an engineered baculovirus fp25k gene that is more mutation resistant. The expression vector of the present invention is more resistant to mutation during the process of producing a desired protein, virus, protein hybrid, or virus hybrid. The engineered baculovirus fp25k gene has one to three modified or mutagenized (or mutated) spots, including two 7-adenine mononucleotide repeats (A7 MNR) and the 10th TTAA site. The first A7 MNR can be referred to as "A7-1" or "A7-1 MNR." Preferably, the A7-1 MNR is modified or mutagenized into AAGAAAA; the second A7 MNR ("A7-2" or "A7-2 MNR") and the 10th TTAA site are collectively mutagenized into CTGAAGAAGA. These are silent mutations. Silent mutations are DNA mutations that do not result in a change to the amino acid sequence of a protein. Other suitable sequences can also be used for the present invention so long as they are silent mutations.

As used herein, the terms "modified" and "mutated" refer to a mutation and/or deletion and/or insertion into the gene and can include genetic events that occur naturally, and/or in a laboratory setting and by design e.g., through cell passaging, and/or through one or more recombinant genetic methods.

Preferably, the A7-1 MNR is mutated by converting AAAAAAA to AAGAAAA to generate an engineered plasmid (a nucleic acid of SEQ ID NO. 7) using a pair of suitable mutagenesis primers. The preferred primers are pA7-1F, 5'-CGA CAG CAG GCT GAA TAA TAA GAA AAT TAG AAA C-3' (a primer of SEQ ID NO. 3), and pA7-1R 5'-CTA ATT TTC TTA TTA TTC AGC CTG CTG TCG TGA ATA CCG-3' (a primer of SEQ ID NO. 4). Other suitable primers can also be used. Suitable primers are the primers that can provide the silent mutations mentioned above.

This plasmid (a nucleic acid of SEQ ID NO. 7) is then used as a template to mutate the A7-2 MNR and the overlapping 10th TTAA site collectively (also called the combined A7-2 MNR and 10th TTAA site) by mutagenizing CTTAAAAAAA to CTGAAGAAGA using suitable primers. After the mutation, the collective site can be referred to as the modified A7-2 MNR/10th TTAA site. The preferred primers are pTTAA-F, 5'-GTT ACT GAA GAA GAC TCG CGA CGC TCT GTT GC-3' (a primer of SEQ ID NO. 5), and pTTAA-R 5'-CGT CGC GAG TCT TCT TCA GTA ACA GCT TTT G-3' (a primer of SEQ ID NO. 6). Other suitable primers can also be used so long as they can provide the silent mutations mentioned above. The resulting engineered plasmid (also called the engineered fp25k gene vector) includes the fp25k gene with three mutated spots (a nucleic acid of SEQ ID NO. 2). In other words, the resulting plasmid vector lost the three mutational "hot spots" of the fp25k gene. In some embodiments of the present invention, the engineered plasmid includes the fp25k gene with one or two mutated spots.

Mutations of AcMNPV fp25k are reported to be caused by slippage replication errors of the two 7-adenine mononucleotide repeats (MNR) and a 287 bp host DNA insertion at the 10th TTAA site in Sf21 cells (Cheng et al., 2013 J. Gen. Virol. 94: 166-176; Gin et al., 2010 J. Gen. Virol. 91: 3053-3064). In Example 1 below, during the Hi5 cell infection, the 287 bp host cellular DNA was also found inserted at the 10th TTAA site at the wt fp25k locus. The other two A7 MNRs might also mutate in Hi5 cells, but were not specifically detected in Example 1.

In some embodiments of the present invention, a recombinant virus with the engineered fp25k gene is generated by co-transfecting Sf9 cells with the engineered fp25k gene vector and viral DNA that contained a gfp expression cassette at the fp25k locus. The recombinant virus is more resistant to mutation. Suitable baculovirus cells can be Hi5 cell, Sf21 cell, Sf9 cell, or a combination thereof.

The method of co-transfecting the virus/plasmid DNA to cell can be found in Cheng et al., 2013, J. Gen. Virol. 94: 166-176, "Reduction of polyhedrin mRNA and protein expression levels in Sf9 and Hi5 cell lines, but not in Sf21 infected with *Autographa californica* multiple nucleopolyhedrovirus fp25k mutants," and in Ogay et al. 2006, Cytotechnology 51, 80-98, both of which are incorporated by reference herein. In the cell transfection method, a monolayer of Sf9 cells in a 30 mm diameter tissue culture dish were co-transfected with 1 μg of engineered fp25k gene vector and 250 ng of viral DNA that contained a gfp expression cassette at the fp25k locus by using polyethylenimine (PEI) (Ogay et al, 2006, Cytotechnology 51, 80-98). Using this method, the resulting recombinant virus contained the engineered fp25k gene but not the gfp expression cassette.

EXAMPLE

The present invention will be described below in more detail. The examples are exemplification only and do not limit the present invention.

Example 1

Wild-type (wt) AcMNPV E2 plaque 3 (AcP3) strain with a nucleic acid of SEQ ID NO. 1 was used for the mutagenesis of the fp25k gene. To eliminate the three hyper-mutational "hot spots," a plasmid transfer vector (pGEMT25k) that contained the wt fp25k gene with about 500 bp flanking sequences on each side of the fp25k gene was used as the template for site-directed mutagenesis using a QuikChange I Site-Directed Mutagenesis Kit (Agilent Technology). The titers of both AcP3 and AcP3SDM were determined by real time qPCR using a pair of AcMNPV pp34 primers (see Cheng et al., 2013 for the method).

Figure 1A:
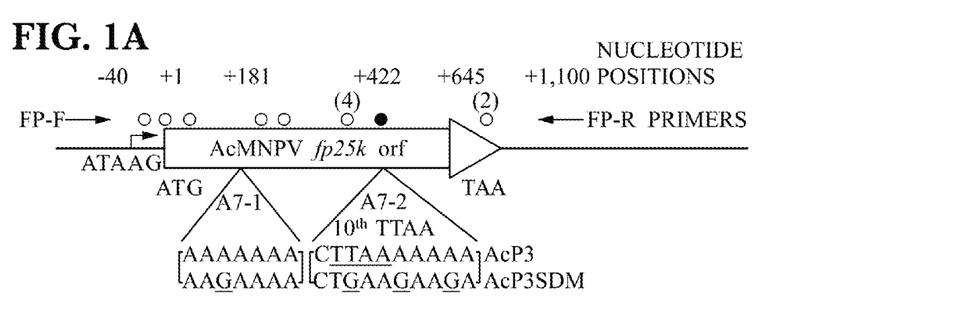
FIG. 1A is a schematic drawing of *Autographa californica* multiple nucleopolyhedrovirus (AcMNPV) fp25k (a nucleic acid of SEQ ID NO. 1) mutational "hot spots" (A7-1, A7-2 and $10^{th}$ TTAA) that are mutagenized into the recombinant baculovirus with a nucleic acid of SEQ ID NO. 2 (also referred to as AcP3SDM). Small circles above the open reading frame (ORF) represent TTAA sites, while the black small circle represents the $10^{th}$ TTAA site. Mutated bases underlined corresponding to that in the wild type AcMNPV (AcP3) with a nucleic acid of SEQ ID NO. 1 are shown in brackets for the engineered fp25k gene of AcP3SDM.

The mutagenesis work was accomplished in a two-step process. First, the A7-1 MNR was mutated by converting AAAAAAA to AAGAAAA to generate a plasmid pUCA7-1 (a nucleic acid of SEQ ID NO. 7) using a pair of mutagenesis primers (pA7-1F, 5'-CGA CAG CAG GCT GAA TAA TAA GAA AAT TAG AAA C-3', a primer of SEQ ID NO. 3, and pA7-1R 5'-CTA ATT TTC TTA TTA TTC AGC CTG CTG TCG TGA ATA CCG-3', a primer of SEQ ID NO. 4) (FIG. 1A). Secondly, the plasmid pUCA7-1 (a nucleic acid of SEQ ID NO. 7) was used as a template to mutate the A7-2 MNR and the overlapping 10th TTAA site by mutagenizing CTTAAAAAAA to CTGAAGAAGA using a pair of primers (pTTAA-F, 5'-GTT ACT GAA GAA GAC TCG CGA CGC TCT GTT GC-3', a primer of SEQ ID NO. 5, and pTTAA-R 5'-CGT CGC GAG TCT TCT TCA GTA ACA GCT TTT G-3', a primer of SEQ ID NO. 6) to generate the pFPSDM plasmid DNA (a nucleic acid of SEQ ID NO. 2) that lost all the three mutational "hot spots" of the wt fp25k gene (FIG. 1A). The pFPSDM plasmid DNA is also referred to as the "transfer vector pFPSDM plasmid DNA" or "pFPSDM plasmid."

To generate a virus with the engineered fp25k gene, a nucleic acid of SEQ ID NO. 2, the transfer vector pFPSDM plasmid DNA and the AcP3Δ25GFP viral DNA that contained a gfp expression cassette at the fp25k locus were used to co-transfect Sf9 cells to generate recombinant viruses that lacked gfp but contained the engineered fp25k gene. In the cell transfection method, a monolayer of Sf9 cells in a 30 mm diameter tissue culture dish were co-transfected with 1 µg of engineered fp25k gene vector and 250 ng of viral DNA that contained a gfp expression cassette at the fp25k locus by using polyethylenimine (PEI). The method of co-transfecting the cell with the AcP3Δ25GFP viral DNA and pFPSDM plasmid DNA can be found in Cheng et al., 2013, J. Gen. Virol. 94: 166-176, "Reduction of polyhedrin mRNA and protein expression levels in Sf9 and Hi5 cell lines, but not in Sf21 infected with Autographa californica multiple nucleopolyhedrovirus fp25k mutants"; and also see Ogay et al, 2006, Cytotechnology 51, 80-98. The recombinant virus AcP3SDM was plaque-purified against the background of gfp expression parental viral plaques to be used in the comparison of fp25k stability in Hi5 cell passage between the parent AcP3 and the recombinant AcP3SDM.

The titers of both AcP3 (a nucleic acid of SEQ ID NO. 1) and AcP3SDM (a nucleic acid of SEQ ID NO. 1) were determined by real time qPCR using a pair of AcMNPV pp34 primers (primers of SEQ ID NO. 11 and SEQ ID NO. 12) (see Cheng et al., 2013 for the method). The engineered viruses AcP3SDM and AcP3 were serially passaged in Hi5 cells according to the method stated in de Rezende et al. except for the modification stated below (de Rezende et al., 2009, J. Invertebr. Pathol. 100: 153-159): Before any passage and at each passage, the inoculum was tittered using real time qPCR. Hi5 cells at the density of 5×105 cells/dish in six well plates were infected with a multiplicity of infection (MOI) of 10 plaque forming units (p.f.u)/cell using BV (budded virus) produced from a previous cell infection. Polyhedra production through the virus infected cells was monitored by phase contrast microscopy. At day four post infection, the majority of Hi5 cells were infected. The BVs in the media were tittered and harvested for infecting Hi5 cells in the next passage.

Figure 1B:
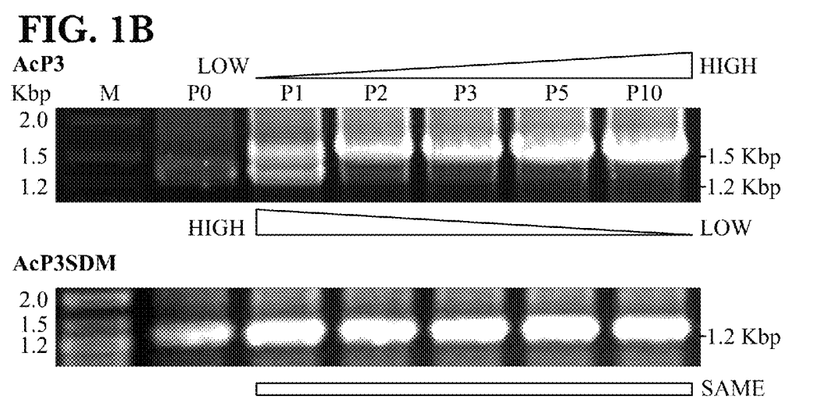
FIG. 1B depicts PCR detection of fp25k gene mutations using DNA templates extracted from the passaged budded viruses (BV) (P1 to P3, P5, and P10) showing increased PCR products of 1.5 kbp and decreased products of 1.2 kbp from the wild-type (wt) AcMNPV E2 plaque 3 (AcP3) strain (a nucleic acid of SEQ ID NO. 1). On the other hand, no change of the 1.2 kbp products for the recombinant baculovirus AcP3SDM (a nucleic acid of SEQ ID NO. 2) is detected. P0 is non-passaged virus stock; P4 and 6 to 9 are not shown.

A total of 10 passages were conducted for PCR analysis of the fp25k stability (see FIG. 1B). For the PCR analysis, an equal volume of the virus-containing medium (300 µl) from each passage was used for viral DNA extraction, and the extracted DNA was dissolved in 10 µl of water. In the PCR analysis of fp25k mutations, a pair of FP primers (FP-F, 5'-ATGCATAGCAATGTCTTC-3', a primer of SEQ ID NO. 8, and FP-R, 5'-TTTACGCACCATATACGC-3', a primer of SEQ ID NO. 9) and the high fidelity pfu DNA polymerase together with 1 µl of each viral DNA from passaged viruses (either from AcP3 or AcP3SDM) were used. The amplified PCR products were analyzed by gel electrophoresis (0.7% agarose running at 90 V for 50 min in TAE buffer), and the resolved DNA products were recovered and directly sequenced. The PCR amplification of the fp25k locus showed in FIG. 1B that at the wt fp25k locus, in addition to the expected 1.2 kbp product, a 1.5 kbp product was found, suggesting the host DNA insertion had occurred.

Figure 1C:
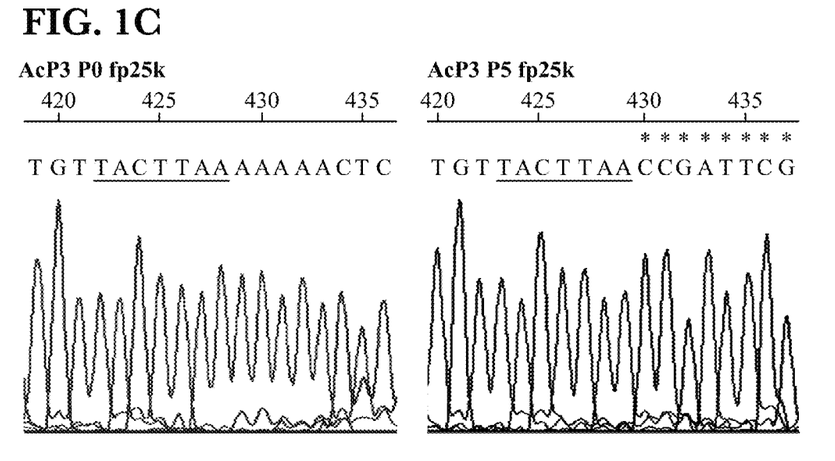

At passage 1, about 50% of progeny viruses had the host DNA insertion (1.5 kbp PCR product) in the fp25k gene, which suggests that the host DNA insertion occurred at a high frequency. After five passages of the viruses, almost all of the progeny viruses had the host DNA insertions (FIG. 1B). The intensity of the 1.5 kbp PCR product also continued to increase from passage 1 until passage 5 and then leveled off, reflecting the increased budding of viral progeny into the media. The increased budding of viral progeny is one hallmark of the fp25k mutation phenotype (Harrison et al., 1995 J. Gen. Virol. 76(Pt 6): 1451-1459; Kelly et al., 2008 Virus. Res. 133: 157-166; Wu et al., 2005 J. Gen. Virol. 86: 2439-2444). When the 1.5 kbp PCR product of wt AcP3 passage 5 was sequenced (a nucleic acid of SEQ ID NO. 10), the only mutation found was the host DNA insertion at the 10th TTAA site, and no other mutation in AcMNPV fp25k was found (please see FIG. 1C).

In the engineered fp25k gene of the AcP3SDM with a nucleic acid of SEQ ID NO. 2 after ten passages, no host DNA insertion was found and no increase in progeny virus budding, indicating that there was no other fp25k mutations (FIG. 1B). Sequencing the PCR products from passage 5 of AcP3SDM confirmed the identity of the engineered fp25k gene. There is also no difference in the yield of the polyhedrin in Hi5 cell infection among passages 1 to 10 of AcP3SDM. These data suggest that the engineered fp25k gene of AcMNPV maintained a higher stability, leading to higher polh promoter activities and higher protein expression yields than that of the AcMNPV with a wt fp25 gene during Hi5 cell infection.

This example demonstrates the improved stability of the engineered AcMNPV fp25k gene (a nucleic acid of SEQ ID NO. 2) over that of the wt fp25k gene (a nucleic acid of SEQ ID NO. 1) during the Hi5 cell passaging. The fp25k gene of other baculoviruses, such as the commercial Bacmid (Invitrogen) and flashBAC™ (BioNovus Life Sciences) can also be similarly engineered to increase protein stability during cell infection.

While not wishing to be bound by theory, it is presently believed that insertion of the 287 bp Hi5 host DNA fragment at the $10^{th}$ TTAA site of the fp25k gene is likely carried out by the Hi5 transposase via a transposition reaction. It also appears that Hi5 transposase was highly active so that about 50% of the BV from passage 1 carried the 278 bpHiS DNA insert (FIG. 1B). Even though high MOI infection was used in this example, the high transposase activity may suggest that even at low MOIs, such as 0.1 or 0.01, the Hi5 transposase may also insert the 287 bp Hi5 host DNA into the fp25k gene to inactivate the 25K protein and thus reduce the polh promoter power, which results in the reduction of protein expression yield. Therefore, blocking the function of the Hi5 transposase may reduce the possibility of the insertion of the host DNA into the fp25k gene, leading to an increased yield of protein expression.

Example 2

This study evaluated whether the engineered fp25k gene of AcMNPV can lead to a higher protein expression yield than that of the AcMNPV with a wt fp25 gene during Hi5 cell infection.

Wild-type (wt) AcMNPV E2 plaque 3 (AcP3) strain (SEQ ID NO.1) was used. The engineered fp25k gene of AcMNPV, a nucleic acid of SEQ ID NO.2, was produced according to the procedures listed in Example 1.

Polyhedra Harvesting:

Hi5 cells were seeded at $5 \times 10^5$ cells/well in six-well plates. BVs of AcP3 passages 1, 5 and 10 as well as AcP3SDM passages 1, 5, and 10 were tittered by the end-point dilution method. In this end-point dilution tittering method, Sf9 cells in 60-well plates were infected with 10 serial dilutions (10 fold each) of the virus stocks. The numbers of wells with infected cells were counted to estimate the dilution of virus that produced infection in 50% of wells (O'Reilly, D. R., Miller, L. K. & Luckow, V. A. (1992). Baculovirus Expression Vectors: a Laboratory Manual. New York: W. H. Freeman & Co.). The Hi5 cells were then infected with the respective virus (AcP3 or AcP3SDM) at a multiplicity of infection (MOI) of 1 virus/cell in triplicate.

At four days post infection, the media that contained BVs from the infected Hi5 cells were withdrawn. The cells were lysed with 1 ml of 0.5% Sodium Dodecyl Sulfate (SDS) for 30 minutes with rocking at 4 rocks/min at room temperature to release polyhedra from cells. Success of complete cell lyses was confirmed by microscopy. The released polyhedra were washed four times in 1 ml of 0.5% SDS by centrifugation at 16,100×g for 1 min. The final polyhedra pellet was washed with sterile water to produce the purified polyhedra.

Figure 2A:
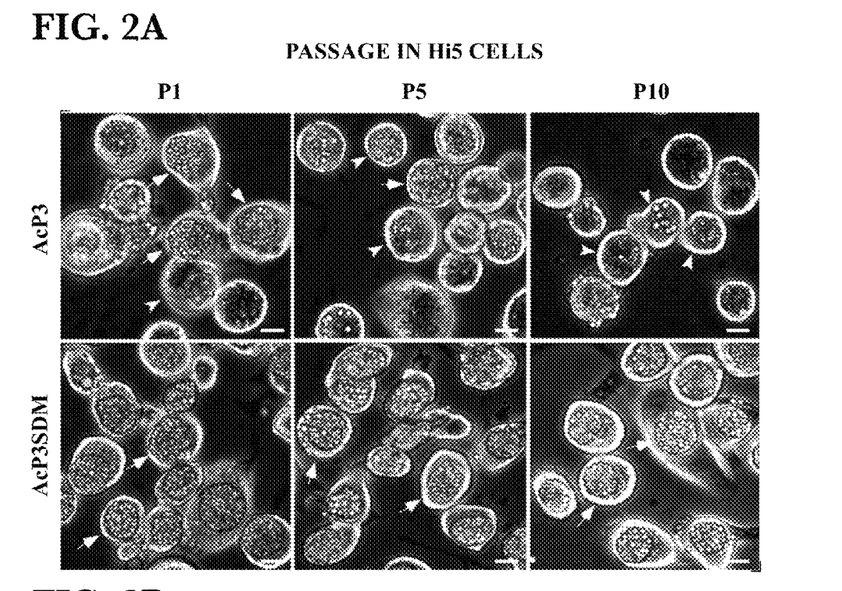
FIG. 2A refers to photographs illustrating polyhedra production between the cells infected with AcP3 (a nucleic acid of SEQ ID NO. 1) and the cells infected with AcP3SDM (a nucleic acid of SEQ ID NO. 2) during Hi5 cell passage. "Arrow heads" point to cells with poor polyhedra product. "Arrows" point to cells with good polyhedra production.
Figure 2B:
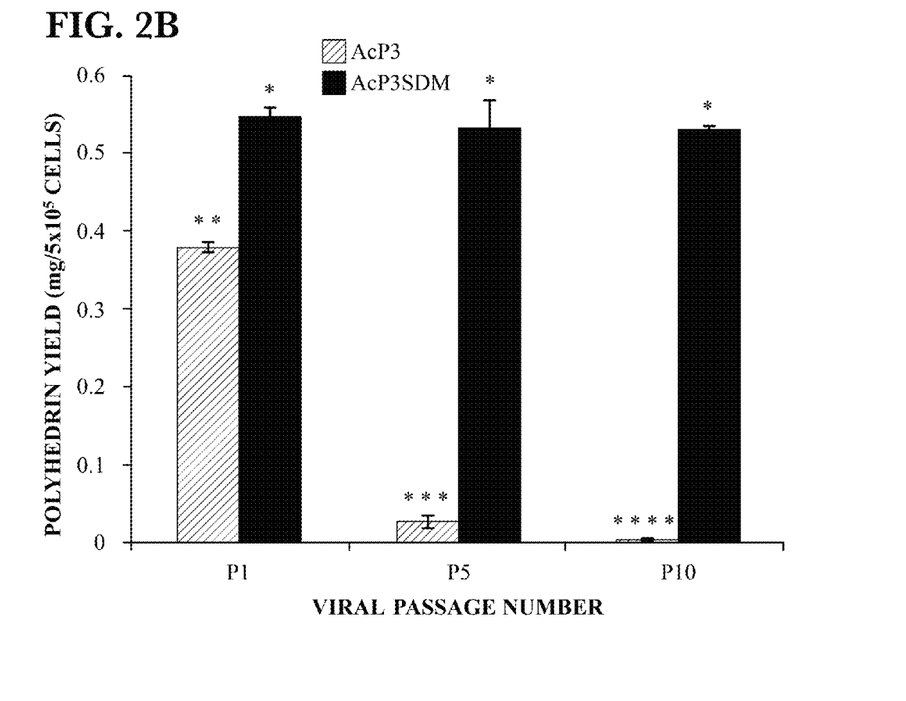
FIG. 2B is a diagram comparing polyhedrin protein yields between the cells infected with AcP3 (a nucleic acid of SEQ ID NO. 1) and the cells infected with AcP3SDM (a nucleic acid of SEQ ID NO. 2) during Hi5 cell passage. Error bars denote standard deviation (SD); n=3. Treatments with different number of asterisk indict significant differences at P≤0.05. Bars, 10 μm.

Polyhedra Protein Measurement:

The purified polyhedra were solubilized by treatment with 1 ml of 0.1 M $Na_2CO_3$ solution (pH 10.5) at 37° C. for 30 min or until no pellet was seen after centrifuging at 16,100× g for 1 min. Polyhedrin yields were estimated by the Bradford method using a Bio-Rad protein assay system. The purified bovine serum albumin (BSA) was used as a standard. The 1× dye reagent solution (2 ml) was added to a glass tube. Forty μl of each diluted BSA in 0.1 M $Na_2CO_3$ solution (0.2, 0.4, 0.6 and 0.9 mg/ml) and unknown samples were added to individual glass tubes with dye and mixed. The mixed protein/dye solutions were incubated at room temperature for 5 minutes. The spectrophotometer was set to 595 nm. The absorbance of the standard and unknown samples was measured. A standard curve by plotting the 595 nm values (y-axis) versus their concentration of BSA in μg/ml (x-axis) was constructed. The unknown sample concentrations were estimated using the standard curve. In this procedure, the unknown samples refer to the purified polyhedrin from AcP3 and AcP3SDM. The polyhedrin yields were then compared between that of AcP3 and that of AcP3SDM (FIGS. 2A and 2B).

Results: The results (FIG. 2A and FIG. 2B) show that there was a progressive reduction of polyhedron during AcP3 passage whereas there was no detectable reduction of polyhedron of AcP3SDM in Hi5 cell passage.

Example 3

This example evaluated the stability of the engineered fp25k gene of AcMNPV_in sf9 cell passage. The stability of the engineered fp25k gene is shown through the maintained or increased yield of polyhedrin protein. Wild-type (wt) AcMNPV E2 plaque 3 (AcP3) strain (a nucleic acid of SEQ ID NO. 1) was used. The engineered fp25k gene of AcMNPV (a nucleic acid of SEQ ID NO. 2) was produced according to the procedures listed in Example 1.

Figure 3A:
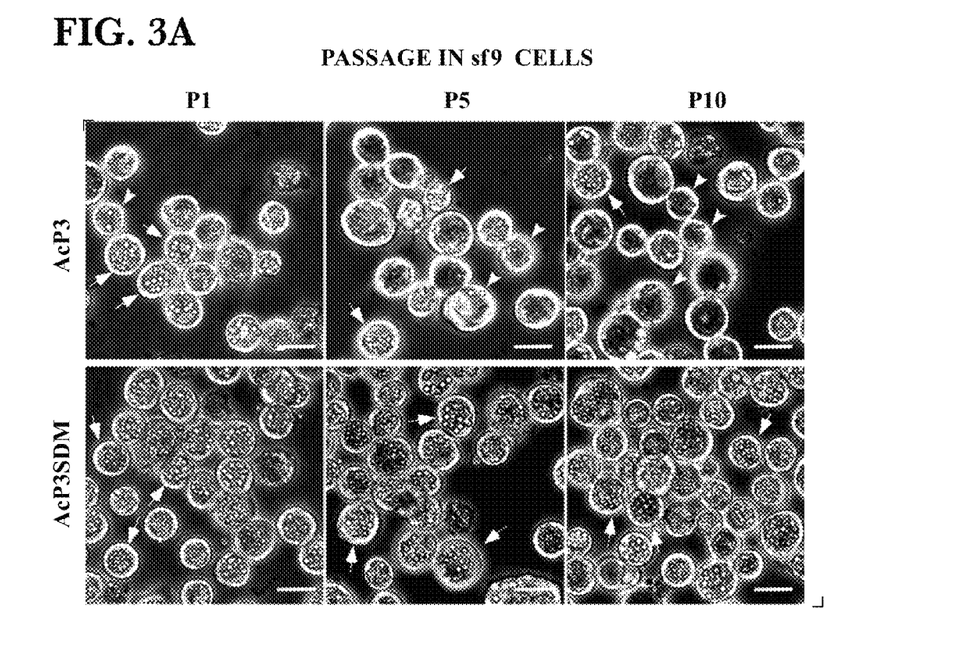
FIG. 3A refers to photographs illustrating polyhedra production between the cells infected with AcP3 (a nucleic acid of SEQ ID NO. 1) and the cells infected with AcP3SDM (a nucleic acid of SEQ ID NO. 2) during Sf9 cell passage. "Arrow heads" point to cells with poor polyhedra product. "Arrows" point to cells with good polyhedra production.
Figure 3B:
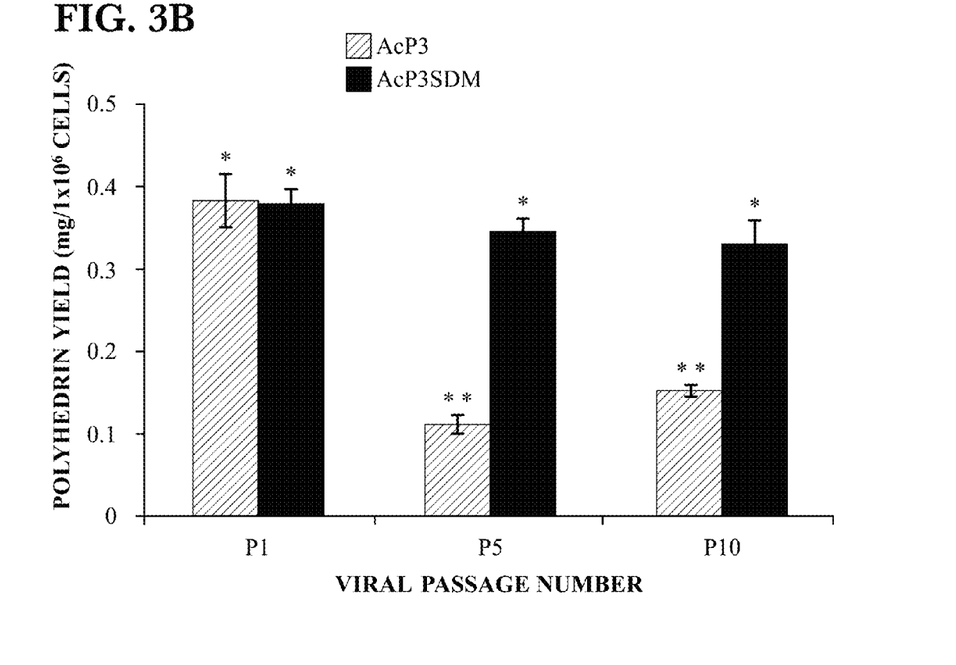
FIG. 3B is a diagram comparing polyhedrin protein yields between the cells infected with AcP3 (a nucleic acid of SEQ ID NO. 1) and the cells infected with AcP3SDM (a nucleic acid of SEQ ID NO. 2) during Sf9 cell passage. Error bars denote standard deviation (SD); n=3. Treatments with different number of asterisk indict significant differences at P≤0.05. Bars, 10 μm.

Sf9 cells were seeded at $1 \times 10^6$ cells/well in six-well plates. The procedures of polyhedrin harvesting and polyhedrin protein measurement were performed according to the procedures listed in Example 2. The results are shown in FIGS. 3A and 3B, and are similar to that of Example 2: There was a progressive reduction of polyhedron during AcP3 passage whereas there was no detectable reduction of polyhedrin of AcP3SDM in Sf9 cell passage.

This detailed description in connection with the drawings is intended principally as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention and that various modifications may be adopted without departing from the invention or scope of the following claims.

The invention claimed is:

1. A recombinant baculovirus expression vector, comprising an engineered baculovirus fp25k gene, which comprises a nucleic acid of SEQ ID NO. 2.

2. The vector of claim 1, wherein the sequence set forth by SEQ ID NO: 2 is modified at nucleotide sequence 181-187 to AAGAAAA and nucleotide sequence 421-430 to CTGAAGAAGA.

3. The vector of claim 1, wherein the baculovirus is an *Autographica californica* multiple nucleopolyhedrovirus (AcMNPV) with a nucleic acid of SEQ ID NO. 1.

4. A recombinant baculovirus cell comprising the engineered baculovirus fp25k gene of claim 1.

5. A method of preparing a baculovirus vector suitable for production of a gene product in a host cell, the baculovirus vector being an engineered baculovirus fp25k gene of a nucleic acid of SEQ ID NO. 2, comprising the steps of:

providing a plasmid that contains the wild-type fp25k gene modifying nucleotide sequence 181-187 of the wild-type fp25k gene to AAGAAAA to produce a first modified plasmid of SEQ ID NO. 7; and using the first modified plasmid of SEQ ID NO. 7 as a template to modify nucleotide sequence 421-430 to CTGAAGAAGA with one or more primers to generate the engineered baculovirus fp25k gene of SEQ ID NO. 2.

6. A method of preparing a recombinant baculovirus with the engineered baculovirus fp25k gene of claim 1, comprising the steps of providing one or more baculovirus cells, and
co-transfecting the baculovirus cells with the engineered baculovirus fp25k gene and a viral DNA with a gfp expression cassette at the fp25k locus.

* * * * *